United States Patent
Orjales et al.

[11] Patent Number: 5,877,187
[45] Date of Patent: Mar. 2, 1999

[54] BENZIMIDAZOLE DERIVATIVES WITH ANTIHISTAMINIC ACTIVITY

[75] Inventors: Aurelio Orjales, Neguri; Victor Rubio, Getxo; Maravillas Bordell, Leioa, all of Spain

[73] Assignee: Fabrica Española de Productos Quimicos y Farmaceuticos S.A. (FAES), Lejona, Spain

[21] Appl. No.: 868,743

[22] Filed: Jun. 4, 1997

[30] Foreign Application Priority Data

Jun. 4, 1996 [ES] Spain ...................................... 9601236

[51] Int. Cl.$^6$ ........................ A61K 31/445; C07D 401/04
[52] U.S. Cl. ............................................. 514/322; 546/199
[58] Field of Search ............................. 546/199; 514/322

[56] References Cited

PUBLICATIONS

Orjales et al, "Synthesis and structure–activity, etc" CA 124:8747, 1995.

*Primary Examiner*—Patricia L. Morris

*Attorney, Agent, or Firm*—Lackenbach Siegel Marzullo Aronson & Greenspan

[57] ABSTRACT

New benzimidazole derivatives of formula:

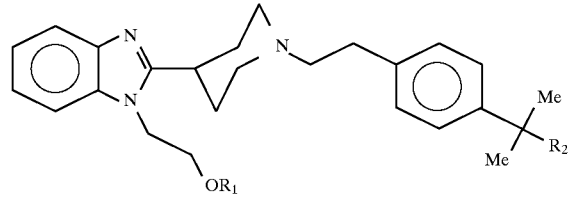

in which $R_1$ is H or a short chain hydrocarbon group such as methyl, ethyl, isopropyl, cyclopropyl, vinyl, etc., and $R_2$ is a group selected from among the following: $CH_2OH$, COOH, $COOR_3$ and 4,4-dimethyl-2-oxazolinyl, $R_3$ being a short chain alkyl group such as methyl, ethyl, etc., are described.

A description is also made of the preparation of these compounds, which have a high $H_1$ antihistaminic and antiallergic activity and are devoid of effects on the central nervous and cardiovascular systems.

22 Claims, No Drawings

BENZIMIDAZOLE DERIVATIVES WITH ANTIHISTAMINIC ACTIVITY

OBJECT OF THE INVENTION

The present invention relates to new benzimidazole derivatives with $H_1$ antihistaminic activity, lacking cardiotoxic effects.

BACKGROUND OF THE INVENTION

The prior art closest to the compounds of the present invention is in Spanish patent No. 9201512 which describes a number of piperidine benzimidazole derivatives with antihistaminic and antiallergic activity of general formula

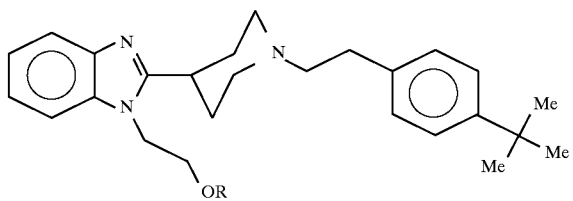

The major structural difference between the compounds of the present invention and those of the said patent is the presence of oxygenated functions in the phenyl group substitution. An important pharmacophorous character has moreover been found for these oxygenated functions which consists essentially in a selectivity of action and provides a pharmacological profile distinct from that of other known antihistimaines. The compounds disclosed in this invention present an almost exclusive $H_1$ antihistaminic pharmacological activity and are therefore devoid of action on other pharmacological receptors even at doses much higher than the therapeutic ones. Because of this selectivity in action, they are valuable instruments in treating allergic-type conditions, particularly allowing their unrestricted use by persons under any other concomitant medication whatsoever, and in the case of patients with pathological cardiocirculatory disturbances.

DESCRIPTION OF THE INVENTION

It has long since been known that histamine plays a very important role in allergic-type diseases, such as allergic rhinitis, conjunctivitis, urticaria and asthma; antihistaminic compounds acting at the $H_1$-receptor histamine level are useful for treating such conditions.

First generation $H_1$ antihistamines presented a number of adverse effects, such as sedation and dryness of the mouth, resulting from its action on the central nervous system and colinergic receptors.

The search for molecules that would not cross the haematoencephalic barrier brought about the displacement of the early antihistamines by other second generation antihistamines which overcame the side effects linked to their action on the central nervous system. This new generation of antihistamines, amongst which noteworthy, due to their extensive use worldwide, are terfenadine and astemizole, has recently displayed a negative aspect in the form of dangerous cardiovascular effects, extending the QT space and ventricular arrhythmia, which has required its use to be avoided in those cases in which the patient is prone to suffering such disturbances or when he is being treated with substances that may interfere with his metabolism.

Attempts at obtaining safe and efficient $H_1$ antihistamines have multiplied in recent years and this research has resulted in several recent patent applications claiming pharmaceutical compositions for treating allergic diseases containing antihistamines devoid of arrhythmogenic effects, which is the case of U.S. patent application Ser. No. 924,156 (Mar. 8, 1992) and international patent application number 95/00480 (May 1, 1995).

The present invention relates to a group of new compounds with benzimidazolic structure having potent selective $H_1$ antihistaminic activity, lacking activity on the central nervous system and on the cardiovascular system.

The compounds subject of the present invention have the following general formula:

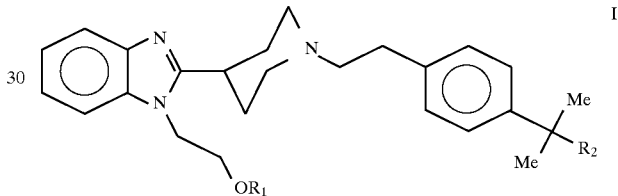

in which $R_1$ is hydrogen or a short chain hydrocarbon group such as methyl, ethyl, isopropyl, cyclopropyl or vinyl, and $R_2$ is a group selected from among $CH_2OH$, $COOH$, $COOR_3$ and 4,4-dimethyl-2-oxazolinyl, $R_3$ being a short chain alkyl group as previously defined, and their addition salts with pharmacologically acceptable acids or bases.

Compounds I in which $R_1$ in a short chain alkyl group and $R_2$ is the 4,4-dimethyl-2-oxazolinyl group can be conveniently prepared by an N-alkylation reaction of 2-(4-piperidinyl)-1H-benzimidazole with an alkylating agent of formula III wherein X is a good leaving group in nucleophilic substitution reactions such as Cl, Br, I, $R_4SO_2$, $R_2SO_3$, etc., in the presence of an inorganic base, such as an alkaline metal carbonate or bicarbonate within an organic solvent, followed by another N-alkylation reaction of the resulting benzimidazole IV with an ether of formula $XCH_2CH_2OR_1$, wherein X has the meaning given above and $R_1$ is a short chain hydrocarbon group, such as Me, Et, i-Pr, cyclopropyl, vinyl, etc., in the presence of a hydride or an alkaline metal carbonate.

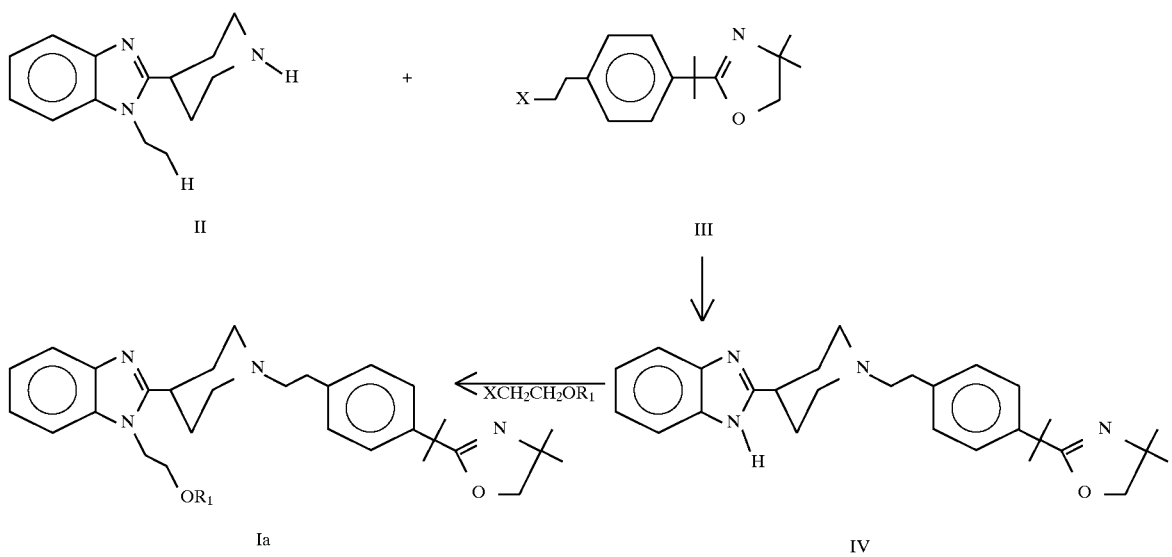

Compounds I, in which $R_1$ is a short chain alkyl group and $R_2$ is a carboxyl group, can be conveniently prepared by hydrolysis of the benzimidazoles Ia with a mineral acid such as HCl or $H_2SO_4$.

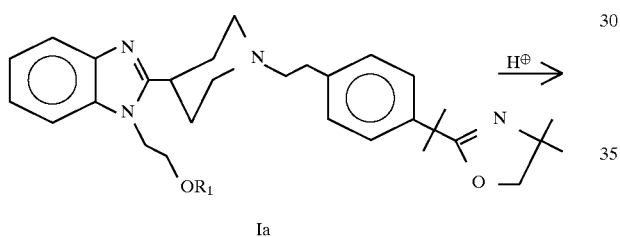

Compounds I in which $R_1$ is a short chain alkyl group and $R_2$ is a $COOR_3$ group in which $R_3$ is a short chain alkyl group, can be prepared by acid hydrolysis of the benzimidazoles Ia in the presence of an alcohol solvent $R_3OH$, in adequate conditions for transesterification.

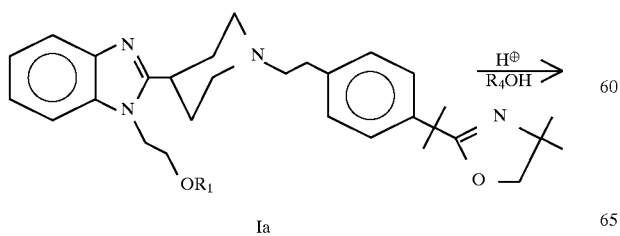

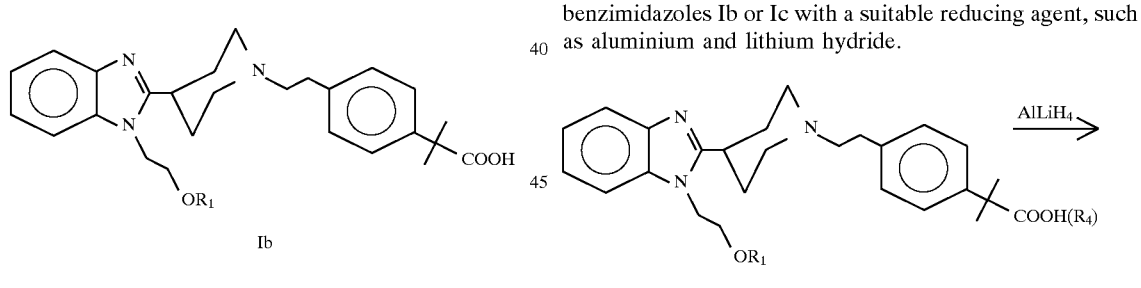

Compounds I in which $R_1$ is a short chain alkyl group and $R_2$ is a $CH_2OH$ group can be prepared by a reduction of the benzimidazoles Ib or Ic with a suitable reducing agent, such as aluminium and lithium hydride.

Compound I in which $R_1$ is a hydrogen and $R_2$ is a 4,4-dimethyl-2-oxazolinyl group can be prepared by an alkylation of the benzimidazole IV with ethyl chloroacetate in the presence of a hydride or an alkaline metal carbonate to yield the ester V, which is then reduced by a reducing agent such as aluminium and lithium hydride.

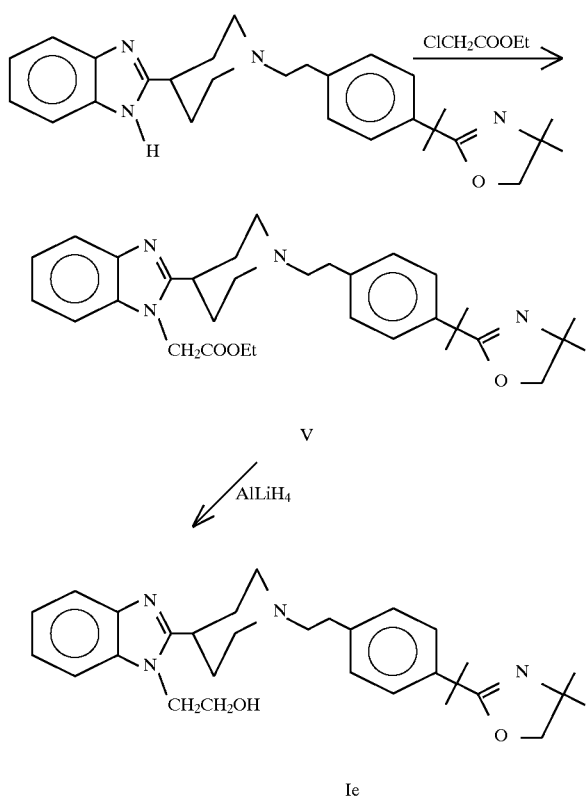

Compound I in which R₁ is a hydrogen and R₂ is a COOH group is conveniently prepared by hydrolysis with a mineral acid such as HCl or $H_2SO_4$ of the compound Ie.

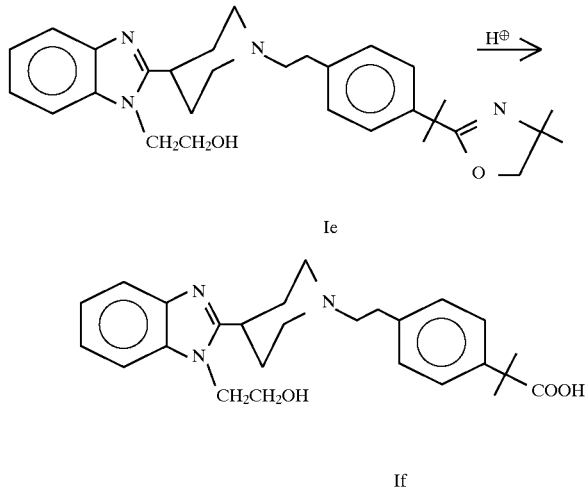

The obtained new benzimidazoles I can be turned into pharmaceutically acceptable salts by treatment with suitable acids or bases.

Compounds of formula I have useful pharmacological properties. In particular, they are potent $H_1$ antihistamines. This activity was clearly demonstrated in vitro by blocking the histamine-induced contractions in the isolated guinea pig ileum (Magnus, Pflügers, Arch. Ges. Physiol., 102, 123 (1904); Arunlakshana, O. and Schild, H. O., Br. J. Pharmacol. 14, 48–58 (1959)) and in vivo by the capacity to inhibit the increment of histamine-induced cutaneous capillary permeability in rats (Lefèbvre, P., Salmon, J., Leconte and Cauwenberge, V. H., C. R. Soc. Biol. 156, 183–186 (1962); Udaka, K., Takeuchi, Y. and Morat, H. Z., Proc. Soc. Exp. Biol. Med. 133, 1384–1387 (1970)).

Thus, compound Ib ($R_1$=ethyl) proved to be potent guinea pig ileum $H_1$-receptor histamine mixed antagonist, with calculated $pA_2$=7.98–8.10 and $pD_2'$=6.50. This same compound inhibited in vivo the increase in capillary permeability in rats with a $DE_{50}$ close to 2 mg/kg p.o. At doses of 5 mg/kg p.o. it maintained a significant activity, in excess of 50%, for at least 6 hours.

These compounds are highly selective in their pharmacological action, and present no significant anticholinergic activity nor activity on the central nervous and cardiovascular systems. Thus, compound Ib ($R_1$=Et) is not able to antagonize significantly the acetylcholine-induced contractions in isolated guinea pig ileum at 0.1M concentrations and does not modify the spontaneous motor activity of the rat at 100 mg/kg p.o.; furthermore, this same compound, administered at 20 mg/kg i.v., induces no morphological ECG disturbance nor does it increase the $QT_c$ interval in rats.

In view of their useful pharmacological antihistaminic and antiallergic properties, the compounds described in the present invention can be formulated in several pharmaceutical forms to be later administered orally, topically, injectably and rectally. Oral preparations are made by intimately mixing a quantity effective as antihistaminic of one of the products described in the present invention with excipients such as lactose, cellulose, talc and the like for tablets or capsules, or water, glycols, alcohols, oils and the like for syrups, solutions and suspensions. Topical administration can be made in the form of creams, ointments, gels, solutions and transcutaneous plasters, using agents such as vaseline, polyethylene glycols, etc. as a carrier. In preparations for injectables, the excipient will be, at least for the most part, sterilised water, although other excipients, such as saline solutions, glucose solutions, etc., or mixtures thereof, may be added to enhance solubility.

The examples detailed below illustrate the present invention without howsoever limiting its scope.

EXAMPLE 1

Preparation of 1-(2-ethoxyethyl)-2-[1-(2-(4-(1-(4,4-dimethyl-Δ²-oxazoline-2-yl)-1-(methylethyl)phenyl)ethyl)piperidine-4-yl]-1H-benzimidazole (Ia, $R_1$=Et)

3.57 g of sodium carbonate were added to a suspension of 14 g 2-(4-(1-(4,4-dimethyl-Δ²-oxazoline-2-yl)-1-methylethyl)phenyl)ethyl p-toluenesulphonate and 6.78 g 2-(4-piperidinyl)-1H-benzimidazole in 60 ml of DMF and the resulting suspension was heated at 80° for 14 hours. The DMF was concentrated and the reaction mass was poured onto water/ice whereupon a solid crystallised which was filtered, washed with water and dried at 50° C. to yield 10 g of 2-[1-(2-(4-(1-(4,4-dimethyl-Δ²-oxazoline-2-yl)-1-methylethyl)phenyl)ethyl)piperidine-4-yl]1H-benzimidazole. The resulting solid was dissolved in 25 ml of DMF and 1.2 g of a sodium hydride in 60% oil suspension was added to this. The resulting suspension was stirred at room temperature for two hours and 2.44 g of 2-chloroethylethylether were added. The reaction mass was heated at 80° C. for 16 hours, cooled, poured on water/ice, extracted with ether and washed with water and with saturated sodium chloride solution. The ethereal solution was dried over anhydrous sodium sulphate and concentrated to yield 11.2 g of 1-(2-ethoxyethyl)-2-[1-(2-(4-( 1-(4,4-dimethyl-Δ²-oxazoline-2-yl)-1-methylethyl)phenyl)ethyl) piperidine-4-yl]-1H-benzimidazole.

MP: 98°–100° C. (ethanol).

RMN-$^1$H (CDCl$_3$), δ: 1.1 (t, 3H); 1.3 (s, 6H); 1.5 (s, 6H), 1.9 (m, 2H); 2.1 (m, 4H); 2.6 (t, 2H); 2.8 (t, 2H); 3.0 (m, 1H); 3.1 (d, 2H); 3.4 (c, 2H); 3.7 (t, 2H); 3.9 (s, 2H); 4.3 (t, 2H); 7.1–7.3 (m, 7H); 7.7–7.8 (m, 1H).

RMN-$^{13}$C (CDCl$_3$), δ: 14.96; 27.38; 28.15; 31.06; 33.10; 34.53; 40.18; 43.60; 53.71; 60.46; 66.74; 66.83; 68.59; 79.14; 109.09; 119.41; 121.71; 121.88; 125.30; 128.73; 134.78; 138.72; 142.72; 143.04; 158.41 and 177.70.

EXAMPLE 2

Preparation of 2-[4-(2-(4-(1-(2-ethoxyethyl) benzimidazole-2-yl)piperidine-1-yl)ethyl)phenyl]-2-methylpropanoic Acid, (Ib, R$_1$=Et)

6.72 g of 1-(2-ethoxyethyl)-2-[1-(2-(4-(1-(4,4-dimethyl-Δ$^2$-oxazoline-2-yl)-1-methylethyl)phenyl)ethyl)piperidine-4-yl]-1H-benzimidazole (Ia) were dissolved in 170 ml of HCl 3N and refluxed for an hour. This was cooled and taken to pH 7 with 50% sodium hydroxide. The solution was extracted with n-butanol, washed with water, dried over anhydrous sodium sulphate and concentrated. Methanol (30 ml) and 50% sodium hydroxide (40 ml) were added to the residue and refluxed for thirty minutes. The methanol was distilled off and water was added until dissolution was complete. This was extracted with ether and the aqueous layer was taken to pH 7 with 20% HCl and saturated with sodium chloride, whereupon a solid precipitated which was filtered, washed repeatedly with water and dried in a vacuum dryer at 50° C. to yield 3.5 g of 2-[4-(2-(4-(1-(2-ethoxyethyl) benzimidazole-2-yl)piperidine-1-yl)ethyl) phenyl]-2-methylpropanoic acid.

MP: 199°–201° C.

RMN-$^1$H (DMSO-d$_6$), δ: 1.0 (t, 3H); 1.4 (s, 6H); 1.8 (m, 4H), 2.2 (m, 2H); 2.5 (t, 2H); 2.7 (t, 2H); 3.0 (m, 3H); 3.3 (c, 2H); 3.6 (t, 2H); 4.4 (t, 2H); 7.0–7.3 (m, 6H); 7.4–7.6 (m, 2H).

RMN-$^{13}$C (DMSO-d$_6$), δ: 14.90; 26.59; 30.97; 32.22; 33.39; 43.04; 45.50; 53.08; 60.05; 65.70; 68.43; 110.18; 118.40; 121.16; 121.35; 125.47; 128.42; 134.72; 138.33; 142.29; 143.03; 158.60; and 177.87.

EXAMPLE 3

Preparation of Ethyl 2-[4-(2-(4-(1-(2-ethoxyethyl) benzimidazole-2-yl)piperidine-1-yl)ethyl)phenyl]-2-methylpropanoate, (Ic, R$_1$=Et, R$_3$=ET)

Concentrated sulphuric acid (20 ml) were added over a solution of 10 g of 1-(2-ethoxyethyl)-2-[1-(2-(4-(1-(4,4-dimethyl-Δ$^2$-oxazoline-2-yl)-1-methylethyl)phenyl)ethyl) piperidine-4-yl]-1H-benzimidazole in 250 ml of ethanol, and this was refluxed for 16 hours. This was cooled and 1 liter of ether was added. The organic layer was separated and washed with water, 10% sodium bicarbonate solution and once again with water. This was dried over anhydrous sodium sulphate and concentrated to yield 7 g of an oil which was purified by flash-chromatography using a 95/5 chloroform/ethanol mixture as eluent to yield 5 g of ethyl 2-[4-(2-(4-(1-(2-ethoxyethyl) benzimidazole-2-yl) piperidine-1-yl)ethyl)phenyl]-2-methylpropanoate in the form of an oil.

RMN-$^1$H (CDCl$_3$), δ: 1.1 (t, 3H); 1.2 (t, 3H); 1.5 (s, 6H); 2.0 (m, 2H); 2.2 (m, 4H); 2.6 (t, 2H); 2.8 (t, 2H); 3.0 (m, 1H); 3.2 (m, 2H); 3.4 (c, 2H); 3.7 (t, 2H); 4.1 (c, 2H); 4.3 (t, 2H); 7.1–7.3 (m, 7H); 7.6–7.7 (m, 1H).

RMN-$^{13}$C (CDCl$_3$), δ: 13.86; 14.80; 26.35; 30.62; 32.73; 33.87; 43.48; 45.91; 53.26; 60.11; 60.49; 66.61; 68.40; 109.02; 119.16; 121.55; 121.75; 125.40; 128.50; 134.56; 138.40; 142.29; 142.51; 158.13 and 176.53.

EXAMPLE 4

Preparation of 1-(2-ethoxyethyl)-2-[1-(2-(4-(1,1-dimethyl-2-hydroxyethyl)phenyl)ethyl)piperidine-4-yl]-1H-benzimidazole, (Id, R$_1$=Et)

1 g of aluminium and lithium hydride was dissolved in 30 ml of THF and 3 g of ethyl 2-[4-(2-(4-(1-(2-ethoxyethyl) benzimidazole-2-yl)piperidine-1-yl)ethyl)phenyl]-2-methylpropanoate were added dropwise thereto. This was stirred for four hours at room temperature and some milliliters of water were added to eliminate excess hydride. The solution was filtered and the filtrate was washed with a saturated sodium chloride solution. This was dried and concentrated. The residue was redissolved in chloroform and washed with water, dried and concentrated. The residue was purified by flash-chromatography using a hexane/ether/isopropyl-amine mixture (2/7.5/0.5) as an eluent, to yield 1.5 g of 1-(2-ethoxyethyl)-2-[1-(2-(4-(1,1-dimethyl-2-hydroxyethyl)phenyl)ethyl)piperidine-4-yl]-1H-benzimidazole.

MP: 112°–114° C.

RMN-$^1$H (CDCl$_3$), δ: 1.0 (t, 3H), 1.4 (s, 6H); 1.9–2.1 (m, 2H); 2.1–2.3 (m, 4H); 2.6 (t, 2H); 2.8 (t, 2H); 3.0 (m, 1H); 3.2 (d, 2H); 3.4 (c, 2H); 3.6 (s, 2H); 3.7 (t, 2H); 4.3 (t, 2H); 7.1–7.4 (m, 7H); 7.8 (m, 1H).

RMN-$^{13}$C (CDCl$_3$), δ: 15.01; 25.34; 31.07; 33.07; 34.53; 39.78; 43.64; 53.72; 60.52; 66.88; 68.62; 73.07; 109.13; 119.44; 121.77; 121.94; 126.22; 128.80; 134.78; 138.39; 142.71; 143.90; 158.45.

EXAMPLE 5

Preparation of 1-(2-hydroxyethyl)-2-[1-(2-(4-(1-(4,4-dimethyl-Δ$^2$-oxazoline-2-yl)-1-methylethyl) phenyl)ethyl)piperidine-4-yl]-1H-benzimidazole, (Ie)

5 g of 2-[1-(2-(4-(1-(4,4-dimethyl-Δ$^2$-oxazoline-2-yl)-1-methylethyl)phenyl)piperidine-4-yl]-1H-benzimidazole were dissolved in 30 ml of DMF and 0.54 g of a sodium hydride in oil suspension were added thereto. The resulting suspension was stirred for two hours at room temperature and 1.19 ml of ethyl chloroacetate were added dropwise. The reaction mass was heated at 70° for 16 hours, cooled and poured on 300 ml of water. This was extracted with ether and the ethereal layer was washed with water, dried over anhydrous sodium sulphate and filtered. 0.8 g of aluminium and lithium hydride were dissolved in 30 ml of ether and the previously filtered ethereal phase was added dropwise to this solution. This was stirred for 4 hours at room temperature, and 20 ml of a 10% sodium hydroxide solution were added thereto. This was saturated with sodium chloride and the ethereal layer was separated. The aqueous phase was extracted with ether. The ethereal phases were all blended together and washed with water and with a saturated sodium chloride solution. This was dried over anhydrous sodium sulphate and concentrated to yield 2.6 g of 1-(2-hydroxyethyl)-2-[1-(2-(4-(1-(4,4-dimethyl-Δ$^2$-oxazoline-2-yl)-1-methylethyl)phenyl)ethyl)piperidine-4-yl]-1H-benzimidazole in the form of an oil.

RMN-$^1$H (CDCl$_3$), δ: 1.3 (s, 6H); 1.6 (s, 6H); 1.8–2.2 (m, 6H); 2.6 (t, 2H); 2.8 (t, 2H); 2.9 (m, 1H); 3.0–3.1 (m, 2H); 3.7 s, 2H); 4.0 (s, 2H); 4.3 (t, 2H); 7.1–7.4 (m, 7H); 7.7 (m, 1H).

RMN-$^{13}$C (CDCl$_3$), δ: 15.01; 25.34; 31.07; 33.07; 34.53; 39.78; 43.64; 53.72; 60.52; 66.88; 68.62; 73.07; 109.13; 119.44; 121.77; 121.94; 126.22; 128.80; 134.78; 138.39; 142.71; 143.90; 158.45.

EXAMPLE 6

Preparation of 2-[4-(2-(4-(1-(2-hydroxyethyl) benzimidazole-2-yl)piperidine-1-yl)ethyl)phenyl]-2-methylpropanoic Acid (If)

5 g of 1-/2-hydroxyethyl)-2-[1-(2-(4-(1-(4,4-dimethyl-Δ$^2$-oxazoline-2-yl)-1-methylethyl)phenyl)ethyl)piperidine-4-yl]-1H-benzimidazole (Ie) were dissolved in 45 ml of 3N HCl and refluxed for an hour. This was taken to a basic pH with 50% NaOH and 20 ml of ethylene glycol were added. This was heated at 190° C. for three hours with simultaneous distillation and then concentrated in vacuo. Water was added and extracted with ether. The aqueous layer was taken to pH 7 with diluted HCl, saturated with sodium chloride and extracted with n-butanol. The ethereal extract was dried and concentrated. The residue was recrystallised in acetone/methanol to yield 2.7 g of 2-[4-(2-(4-(1-(2-hydroxyethyl) benzimidazole-2-yl)piperidine-1-yl)ethyl)phenyl]-2-methylpropanoic acid.

MP: 218° C. (breaks down)

RMN-$^1$H (CDCl$_3$), δ: 1.4 (s, 6H); 2.0–2.1 (m, 4H); 2.7–2.9 (m, 4H); 2.9–3.1 (t, 2H); 3.2–3.5 (m, 3H); 3.7 (t, 2H); 4.3 (t, 2H); 6.9–7.1 (m, 2H); 7.1–7.2 (m, 2H); 7.2–7.3 (m, 2H); 7.3–7.4 (m, 1H); 7.4–7.5 (m, 1H).

We claim:

1. A benzimidazole derivative of the formula:

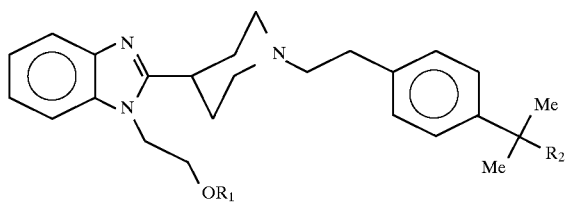

in which R$_1$ is hydrogen or a short chain alkyl group or vinyl, and R$_2$ is a group selected from the group consisting of CH$_2$OH, COOH, COOR$_3$ and 4,4-dimethyl-2-oxazolinyl, R$_3$ being a short chain alkyl group or vinyl, and an addition salt thereof with pharmacologically acceptable acids or bases.

2. A compound in accordance with claim 1 which is 1-(2-ethoxyethyl)-2-[1-(2-(4-(1-(4,4-dimethyl-Δ$^2$-oxazoline-2-yl)-1-methylethyl)phenyl)ethyl)piperidine-4-yl]-1-H-benzimidazole or an addition salt with a pharmaceutically acceptable acid or base.

3. A compound in accordance with claim 1 which is 2-[4-(2-(4-(1-(2-ethoxyethyl)benzimidazole-2-yl) piperidine-1-yl)ethyl)phenyl)phenyl]-2-methyl propanoic acid or an addition salt with a pharmaceutically acceptable acid or base.

4. A compound in accordance with claim 1 which is ethyl 2-[4-(2-(4-(1-(2-ethoxyethyl)benzimidazole-2-yl) piperidine-1-yl)ethyl)phenyl]-2-methylpropanoate or an addition salt with a pharmaceutically acceptable acid or base.

5. A compound in accordance with claim 1 which is 1-(2-ethoxyethyl)-2-[1-(2-(4-(1,1-dimethyl-2-hydroxyethyl)phenyl)ethyl)piperidine-4-yl]-1-H-benzimidazole or an addition salt with a pharmaceutically acceptable acid or base.

6. A compound in accordance with claim 1 which is 1-(2-hydroxyethyl)-2-[1-(2-(4-(1-(4,4-dimethyl-Δ$^2$-oxazoline-2-yl)-1-methyl-ethyl)phenyl)ethyl)piperidine-4-yl]-1H-benzimidazole or an addition salt with a pharmaceutically acceptable acid or base.

7. A compound in accordance with claim 1 which is 2-[4-(2-(4-(1-(2-hydroxyethyl)benzimidazole-2-yl)ethyl) phenyl]-2-methyl propanoic acid or an addition salt with a pharmaceutically acceptable acid or base.

8. An antihistaminic pharmaceutical composition, characterized by the compound claimed in claim 1 as an active ingredient, mixed with one or several excipients.

9. An antihistaminic pharmaceutical composition, characterized by the compound claimed in claim 2 as an active ingredient, mixed with one or several excipients.

10. An antihistaminic pharmaceutical composition, characterized by the compound claimed in claim 3 as an active ingredient, mixed with one or several excipients.

11. An antihistaminic pharmaceutical composition, characterized by the compound claimed in claim 4 as an active ingredient, mixed with one or several excipients.

12. An antihistaminic pharmaceutical composition, characterized by the compound claimed in claim 5 as an active ingredient, mixed with one or several excipients.

13. An antihistaminic pharmaceutical composition, characterized by the compound claimed in claim 6 as an active ingredient, mixed with one or several excipients.

14. An antihistaminic pharmaceutical composition, characterized by the compound claimed in claim 7 as an active ingredient, mixed with one or several excipients.

15. A process for treating allergic diseases in patients, which comprises administering a pharmaceutical composition in accordance with claim 8, an effective amount of active ingredient.

16. A process for treating allergic diseases in patients, which comprises administering a pharmaceutical composition in accordance with claim 9, an effective amount of active ingredient.

17. A process for treating allergic diseases in patients, which comprises administering a pharmaceutical composition in accordance with claim 10, an effective amount of active ingredient.

18. A process for treating allergic diseases in patients, which comprises administering a pharmaceutical composition in accordance with claim 11, an effective amount of active ingredient.

19. A process for treating allergic diseases in patients, which comprises administering a pharmaceutical composition in accordance with claim 12, an effective amount of active ingredient.

20. A process for treating allergic diseases in patients, which comprises administering a pharmaceutical composition in accordance with claim 13, an effective amount of active ingredient.

21. A process for treating allergic diseases in patients, which comprises administering a pharmaceutical composition in accordance with claim 14, an effective amount of active ingredient.

22. A compound in accordance with claim 1, wherein each said alkyl group is at least one selected from methyl, ethyl, isopropyl and cyclopropyl.

* * * * *

UNITED STATES PATENT AND TRADEMARK OFFICE
CERTIFICATE OF CORRECTION

PATENT NO.    : 5,877,187
DATED         : March 2, 1999
INVENTOR(S)   : Orjales et al.

It is certified that error appears in the above-identified patent and that said Letters Patent is hereby corrected as shown below:

Column 3,
Formula II should appear as follows:

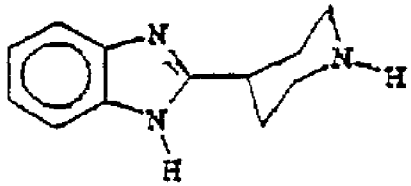

Column 3,
Formula Ia, the portion of the formula reading "R$_4$OH" should read -- R$_3$OH --.

Column 4,
Formula Ib(Ic), the portion of the formula reading "(R$_4$)" should read -- (R$_3$) --.

Column 7,
Line 48, "R3=ET" should read -- R$_3$=Et --.

Column 8,
Line 42, "methylethyl)phenyl)piperidine-4-yl]-1H-benzimidazole" should read
-- methylethyl)phenyl)ethyl)piperidine-4-yl]-1H-benzimidazole --.

Column 9,
Line 55, "piperidine-1-yl)ethyl)phenyl)phenyl]-2-methyl propanoic" should read
-- piperidine-1-yl)ethyl)phenyl]-2-methyl propanoic --.

Signed and Sealed this

Twenty-seventh Day of August, 2002

*Attest:*

JAMES E. ROGAN
*Attesting Officer*        *Director of the United States Patent and Trademark Office*

EX PARTE REEXAMINATION CERTIFICATE (5072nd)

United States Patent
Orjales et al.

(10) Number: US 5,877,187 C1
(45) Certificate Issued: Mar. 1, 2005

(54) BENZIMIDAZOLE DERIVATIVES WITH ANTIHISTAMINIC ACTIVITY

(75) Inventors: Aurelio Orjales, Neguri (ES); Victor Rubio, Getxo (ES); Maravillas Bordell, Leioa (ES)

(73) Assignee: Faes Farma, S.A., Leioa (ES)

Reexamination Request:
No. 90/006,799, Oct. 6, 2003

Reexamination Certificate for:
Patent No.: 5,877,187
Issued: Mar. 2, 1999
Appl. No.: 08/868,743
Filed: Jun. 4, 1997

Certificate of Correction issued Aug. 27, 2002.

(30) Foreign Application Priority Data

Jun. 4, 1996 (ES) .............................. 9601236

(51) Int. Cl.[7] ................ C07D 401/04; A61K 31/445
(52) U.S. Cl. ...................... 514/322; 546/199
(58) Field of Search ........................ 514/322; 546/199

(56) References Cited

U.S. PATENT DOCUMENTS

| | | |
|---|---|---|
| 5,322,850 A | 6/1994 | Orjales-Venero et al. |
| 5,375,693 A | 12/1994 | Woosley et al. |

FOREIGN PATENT DOCUMENTS

| | | |
|---|---|---|
| EP | 0 580 541 A1 | 1/1994 |
| WO | WO 94/03170 A1 | 2/1994 |
| WO | WO 95/00480 A1 | 1/1995 |

OTHER PUBLICATIONS

Ryuichi Iemura et al, "Synthesis of Benzimidazole Derivatives as Potential $H_1$–Antihistaminic Agents", Journal of Heterocyclic Chemistry, vol. 24, Jan.–Feb. 1987, pp., 31–37.

Aurelio Orjales et al, "Synthesis and Structure–Activity Relationship of New Piperidinyl and Piperazinyl Derivatives as Antiallergics", Journal of Heterocyclic Chemistry, vol. 32, No. 3, May–Jun. 1995, pp. 707–718.

*Primary Examiner*—Zinna N. Davis

(57) ABSTRACT

New benzimidazole derivatives of formula:

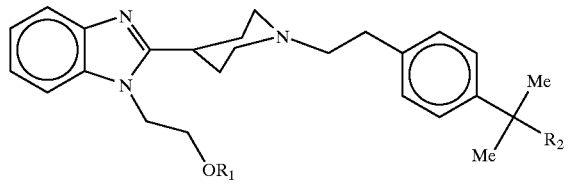

in which $R_1$ is H or a short chain hydrocarbon group such as methyl, ethyl, isopropyl, cyclopropyl, vinyl, etc., and $R_2$ is a group selected from among the following: $CH_2OH$, COOH, $COOR_3$ and 4,4-dimethyl-2-oxazolinyl, $R_3$ being a short chain alkyl group such as methyl, ethyl, etc., are described.

A description is also made of the preparation of these compounds, which have a high $H_1$ antihistaminic and antiallergic activity and are devoid of effects on the central nervous and cardiovascular systems.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–22 is confirmed.

* * * * *